(12) United States Patent
Son (10) Patent No.: US 9,329,167 B2
(45) Date of Patent: *May 3, 2016

(54) REPLACEABLE ALCOHOL SENSOR MODULE

(71) Applicant: AK GLOBALTECH CORP., Palisades Park, NJ (US)

(72) Inventor: Matthew Hogyun Son, Palisades Park, NJ (US)

(73) Assignee: AK GLOBALTECH CORP., Palisades Park, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/878,990

(22) Filed: Oct. 8, 2015

(65) Prior Publication Data

US 2016/0033477 A1    Feb. 4, 2016

Related U.S. Application Data

(63) Continuation-in-part of application No. 14/822,748, filed on Aug. 10, 2015, which is a continuation of application No. 13/559,249, filed on Jul. 26, 2012, now Pat. No. 9,103,818, which is a continuation of application No. 12/955,628, filed on Nov. 29, 2010, now Pat. No. 8,250,900, which is a continuation of application No. 11/528,979, filed on Sep. 27, 2006, now Pat. No. 7,841,224.

(60) Provisional application No. 60/776,127, filed on Feb. 22, 2006.

(51) Int. Cl.
*G01N 33/00* (2006.01)
*G01N 33/497* (2006.01)

(52) U.S. Cl.
CPC .................. *G01N 33/4972* (2013.01)

(58) Field of Classification Search
None
See application file for complete search history.

(56) References Cited

U.S. PATENT DOCUMENTS 5,020,628 A    6/1991  Bigliardi et al.
5,239,492 A    8/1993  Hartwig et al.

FOREIGN PATENT DOCUMENTS

WO    02/077636 A2    10/2002
WO    2005/101281 A2    10/2005

*Primary Examiner* — Robert R Raevis
(74) *Attorney, Agent, or Firm* — Im IP Law PLLC; C. Andrew Im (57) ABSTRACT

A replaceable alcohol sensor module for use with a breathalyzer. The alcohol sensor module requiring calibration can be removed from the body of the breathalyzer and replaced with a new alcohol sensor module. The replaceable alcohol sensor module has at least an alcohol sensor and an adapter that removably connects the replaceable sensor module to the breathalyzer. The adapter transmits the electrical current generated by the alcohol sensor to a processor of the breathalyzer for processing. The alcohol sensor and the adapter are mounted on a printed circuit board to provide the replaceable sensor module.

15 Claims, 8 Drawing Sheets

KEY-CHAIN BREATHALYZER

REPLACEABLE ALCOHOL SENSOR MODULE

RELATED APPLICATION

The present application is a continuation-in-part application of application Ser. No. 14/822,748 filed Aug. 10, 2015, which is a continuation of application Ser. No. 13/559,249 filed Jul. 26, 2012, now U.S. Pat. No. 9,103,818, which is a continuation of U.S. application Ser. No. 12/955,628 filed Nov. 29, 2010, now U.S. Pat. No. 8,250,900, which is a continuation of U.S. application Ser. No. 11/528,979 filed Sep. 27, 2006, now U.S. Pat. No. 7,841,224, which claims the benefit of U.S. Provisional Application Ser. No. 60/776,127 filed Feb. 22, 2006, each of which is incorporated herein by reference in its entirety.

FIELD OF THE INVENTION

The claimed invention relates to a calibrated replaceable alcohol sensor module for use with a Breath Alcohol Testing Device. More specifically, this invention describes an alcohol sensor module that can be removed from the body of a breathalyzer and separately calibrated for the accurate calculation of "percent blood alcohol concentration" (% BAC) based on breath air samples, and then re-installed into the breath alcohol tester.

RELATED ART

The Breath Alcohol Testing Device is also commonly called a "breathalyser" or a "breathalyzer" (hereinafter breathalyzer), and includes both portable (PBT or Portable Breath Tester) and stationary (coin-operated or similar) units.

The availability and accessibility of the breathalyzer for both professional use (as in clinical, industrial, healthcare or workplace settings) and personal use (as in the domain of general consumers) has been expanding greatly, and with this expansion the necessity for all breathalyzers to be periodically recalibrated has created many interruptions in the market, as breathalyzers must currently be mailed or delivered to select service center locations where calibration can be done using a simulation system, making the breathalyzer unavailable to the user during this calibration period, and increasingly overwhelming the service centers as the market grows. The claimed invention remedies this situation by providing a method to calibrate (or re-calibrate) the breathalyzer that greatly reduces or even eliminates the time and cost involved in shipping and handling of breathalyzers and maintenance of service centers, as well as the time and utility lost by the end user.

A typical breathalyzer consists primarily of an alcohol sensor component, signal processing unit (or CPU) 150, and a display unit 140 to show results. Typically, a breath alcohol sensor is calibrated to match select calibration points using standard specifications (controlled alcohol mixtures), and the signal processing unit (or CPU) determines BAC based on linear calculation using the calibration points. Over time (generally after several hundred tests), every breath alcohol sensor will require re-calibration as undesirable residue and foreign substances including, but not limited to, saliva, cigarette smoke residue and food particles, become trapped inside the sensor. The current system of calibration (or re-calibration) of breathalyzers by service centers takes place when a consumer or end user, with a breathalyzer in need of calibration, contacts a breathalyzer retailer. The retailer, in turn, directs the end user to ship the breathalyzer to an appropriate service center location. Upon receiving the breathalyzer, the service center uses controlled alcohol mixtures in order to re-calibrate the device according to standard specifications. When this re-calibration is complete, the breathalyzer is shipped back to the end user. This procedure for re-calibration is time-consuming and costly in terms of shipping and handling of packages, labor hours and lost utility for the end user. There are currently over 100 retailers (online and offline) and/or distributors sell breathalyzer units to consumers and end users, whereas fewer than ten (10) service center locations exist to perform traditional breathalyzer re-calibrations. Due to this discrepancy, the overall increase in sales of breathalyzer units are overwhelming the service centers with requests for re-calibration (which are both necessary and periodic for each breathalyzer), causing ever increasing delays in the processing and delivery of breathalyzers. Another issue resulting from the current system of re-calibration is that the sensor is not actually replaced, and residue buildup cannot be cleaned or removed from the sensor. This results in an increasing deterioration in overall sensor performance as residue accumulates over time, even as the sensor is re-calibrated multiple times.

In order to alleviate the time and utility lost when sending a breathalyzer for re-calibration, some end users purchase multiple breathalyzers so that at least one breathalyzer is available for use while one or more other devices are undergoing service for re-calibration. Some end users cannot afford the increase in budget in order to implement this type of stopgap measure, so compromises are made either in terms of temporary suspension of breath alcohol tests or over-taxing breathalyzer units beyond the point of necessary re-calibration (thereby allowing the breathalyzer to display increasingly inaccurate readings). In many cases, end users elect not to use breathalyzers altogether primarily due to the complications of re-calibration. Re-calibration, though an absolute necessity in the breathalyzer market, is one of the main impediments to rapid expansion of the market, especially in workplace, clinical or other professional environments where both accuracy and continuous utility are required.

Accordingly, the claimed invention proceeds upon the desirability of providing significant benefits for both the breathalyzer service centers and the end users by practically eliminating the loss of time and utility for end users and reducing the number of labor hours and shipping costs for service centers, all while introducing an effective solution at a cost no greater than the current service center system.

OBJECTS AND SUMMARY OF THE INVENTION

Therefore, it is an object of the claimed invention to provide a significantly improved replacement for the traditional method of breathalyzer re-calibration that supports market security by reducing or eliminating the time and utility lost by the end user and that also expands the market by addressing the specific needs of industrial or clinical breathalyzer applications. The claimed invention comprises a calibrated (or calibrate-able) alcohol sensor module, which comprises at least an alcohol sensor and an adapter to provide an electronic link to the breathalyzer to communicate sensor readings. In accordance with an exemplary embodiment of the claimed invention, the calibrated alcohol sensor module additionally comprises a non-volatile memory unit to store calibration information. The calibrated alcohol sensor module of the claimed invention is useable by distributors, retailers, sellers, buyers and end users to replace or eliminate traditional methods of breathalyzer re-calibration with a much more effective and efficient solution at a cost no greater and often less than any current method of re-calibration.

The alcohol sensor module of the claimed invention can be removed from the body of a breathalyzer and separately calibrated for the accurate calculation of "blood alcohol concentration" (BAC) based on breath air samples, and then re-installed into the breath alcohol tester. In accordance with an exemplary embodiment of the claimed invention, the sensor module comprises an alcohol sensor and an adapter to provide an electronic link to the breathalyzer to communicate sensor readings. In accordance with another exemplary embodiment of the claimed invention, the sensor module additionally comprises a non-volatile memory unit (such as EEPROM, Flash drive, NAND) to store calibration information. The claimed invention brings significant benefits the breathalyzer industry by giving consumers and/or other end users a better solution for re-calibrating the breathalyzer.

The claimed invention essentially eliminates the loss of time and utility for end users and reduces the number of labor hours and shipping costs for breathalyzer service centers. The claimed invention brings these significant benefits and solution to both end users and breathalyzer service centers at a cost that is no greater than the current service center system. The calibrated, replaceable alcohol sensor modules of the claimed invention enables the end users to purchase new sensor modules when the need arises at a cost no more than (and often less than) the cost for re-calibration service. New or calibrated sensor modules of the claimed invention ship with simple instructions for the end user to follow in order to manually replace the old sensor module requiring calibration. Because the sensor modules are pre-calibrated, shipment to the end user is immediate and without delay. The end users can purchase sensor modules simultaneously with the purchase of a breathalyzer or prior to the time that the old sensor requires re-calibration. The process of re-calibration with the sensor module of the claimed invention is simpler and faster than the current calibration system of utilizing a breathalyzer service center since the end user only needs to spend a few seconds swapping the old sensor module with a new sensor module in order to return the breathalyzer to its full functional use without delay.

The claimed invention addresses all known and future breathalyzers (or other breath alcohol testing devices) because the replaceable sensor module can be made compatible with current and future breathalyzers (or other breath alcohol testing devices). In accordance with an embodiment of the claimed invention, the replaceable sensor module can be applied with minimal modification to various other portable electronic devices, as long as such devices having a processing unit processing sensor readings and a display capable of showing % BAC readings (e.g. digital LED display), such as portable radar detectors, portable GPS devices, mobile phones, electronic key/keychain devices, etc.

In accordance with an embodiment of the claimed invention, a breathalyzer user (general consumer, owner or operator of a breathalyzer compatible with the claimed invention) can purchase or otherwise acquire a new sensor module in order to replace the old sensor module at minimal cost and time lost for all parties involved when the breathalyzer's sensor requires re-calibration.

The traditional re-calibration system and procedure involves multiple transactions and/or communications among several entities. Typically an end user (general consumer, owner or operator of a breathalyzer) contacts the retailer from which the breathalyzer was purchased in order to report that the breathalyzer is in need of re-calibration. Currently, the large majority of all breathalyzer retailers are unable to perform re-calibration themselves, so either the retailer accepts breathalyzers requiring re-calibration from end users and ships them in bulk to a breathalyzer service center, or the retailer directs the end user to ship the breathalyzer requiring re-calibration directly to the service center. When the service center receives breathalyzers requiring re-calibration, detailed records of receipts, shipments, customer and retailer (vendor) data must be kept and maintained in order to minimize errors in processing and shipping the re-calibrated breathalyzer. Further, any problems that may arise are complicated to resolve, as these problems involve several parties that are not current with the specific situation of the end user (e.g. a single re-calibration may involve a retailer, distributor, service center and end user). With the multiple communications, transactions, record-keeping, processing and shipping that may be involved with each re-calibration, a steady increase in delays, costs and other problems can be seen in the breathalyzer market, because re-calibrations are unavoidable and periodically necessary.

The claimed invention eliminates many of these aforementioned problems associated with the current re-calibration system and methodology by removing entirely the need for record-keeping, processing and shipping of calibrated breathalyzers beyond the common retail practice of stocking the replaceable sensor modules by the retailers and/or distributors. Delays, costs and problems associated with the current re-calibration system can be greatly reduced and even eliminated with the claimed invention. All breathalyzer service centers operate primarily as either breathalyzer distributors or retailers, and the service center portion of business does not generally generate significant income for these distributors or retailers, often creating a loss in profit. The claimed invention seeks to either greatly reduce the strain on the operation of these service centers or eliminate the need for service centers altogether. In addition, by streamlining the transactions between distributors, retailers and end users into effectively "retail only" market channels, the breathalyzer market can be made more efficient and ready for uninterrupted growth. Calibrated replaceable sensor modules of the claimed invention will be made available to all parties involved in the breathalyzer transactions, thereby requiring only a single transaction (sale) with a single party for the end user to re-calibrate a breathalyzer, in most cases.

It is a further object of the claimed invention to afford simple, straightforward instructions for the handling, installation and removal of calibrated replaceable breath alcohol sensor modules to the general consumer so that these operations can be performed with ease.

It is yet another object of the claimed invention to afford additional breath alcohol sensing functionality to a wide array of other portable electronic devices that comprises a processing unit and a display capable of showing BAC readings (e.g. digital LED display). With minimal modification, the claimed invention can be incorporated into such portable electronic devices as portable radar detectors, portable GPS devices, mobile phones, electronic key/keychain devices, etc.

In accordance with an exemplary embodiment of the claimed invention, a replaceable alcohol sensor module for use with a breathalyzer is provided. An alcohol sensor is calibrated to provide an electrical current proportional to an amount of alcohol detected in a breath sample. An adapter removably connects the replaceable sensor module to the breathalyzer and transmits the electrical current generated by the alcohol sensor to a processor of the breathalyzer for processing. The processor of the breathalyzer measures the electrical current and calculates a blood alcohol concentration of the breath sample based on the measured electrical current.

The alcohol sensor and the adapter is mounted on a printed circuit board to provide the replaceable alcohol sensor module for use with the breathalyzer.

In accordance with an exemplary embodiment of the claimed invention, the aforesaid replaceable alcohol sensor module is installable in the breathalyzer to replace existing replaceable alcohol sensor module in the breathalyzer after being used for a predetermined number of times.

In accordance with an exemplary embodiment of the claimed invention, the aforesaid replaceable alcohol sensor module comprises a non-volatile memory unit to store information to maintain the alcohol sensor in a calibrated state.

In accordance with an exemplary embodiment of the claimed invention, the aforesaid replaceable alcohol sensor module comprises a breath sampling tube to receive and direct the breath sample to the alcohol sensor in a calibrated.

In accordance with an exemplary embodiment of the claimed invention, the aforesaid alcohol sensor of the replaceable alcohol sensor module is individually calibrated prior to installation into the breathalyzer.

In accordance with an exemplary embodiment of the claimed invention, the aforesaid replaceable sensor module is replaced with a new replaceable sensor module in response to a determination that the alcohol sensor requires re-calibration.

In accordance with an exemplary embodiment of the claimed invention, the aforesaid breathalyzer is one of the following: a portable breathalyzer, a coin-operated breathalyzer, a key-chain breathalyzer or a car ignition breathalyzer.

In accordance with an exemplary embodiment of the claimed invention, the aforesaid alcohol sensor of the replaceable sensor module is a fuel cell sensor.

In accordance with an exemplary embodiment of the claimed invention, a replaceable alcohol sensor module for use with a breathalyzer is provided. An alcohol sensor that is calibrated to provide a change in its resistivity based an amount of alcohol detected in a breath sample. An adapter removably connects the replaceable sensor module to the breathalyzer and transmits the change in the resistivity of the alcohol sensor to a processor of the breathalyzer for processing. The processor of the breathalyzer calculates a blood alcohol concentration of the breath sample based on the change in the resistivity of the alcohol sensor. The alcohol sensor and the adapter is mounted on a printed circuit board to provide the replaceable alcohol sensor module for use with the breathalyzer.

In accordance with an exemplary embodiment of the claimed invention, the aforesaid replaceable alcohol sensor module is installable in the breathalyzer to replace existing replaceable alcohol sensor module in the breathalyzer after being used for a predetermined number of times.

In accordance with an exemplary embodiment of the claimed invention, the aforesaid alcohol sensor provides an electrical current based the change in the resistivity of the alcohol sensor. The processor of the breathalyzer measures a change in the conductivity of the alcohol sensor based on the electric current to calculate the blood alcohol concentration of the breath sample.

In accordance with an exemplary embodiment of the claimed invention, the aforesaid the alcohol sensor of the replaceable alcohol sensor module is a semiconductor sensor.

In accordance with an exemplary embodiment of the claimed invention, the aforesaid replaceable alcohol sensor module comprises a heating unit to warm up the semiconductor sensor to a predetermined temperature.

In accordance with an exemplary embodiment of the claimed invention, the aforesaid semiconductor sensor is warmed up to a predetermined temperature by a heating unit of the breathalyzer.

In accordance with an exemplary embodiment of the claimed invention, a breathalyzer comprises a processor, a replaceable alcohol sensor module, a display and a housing. An alcohol sensor of the replaceable alcohol sensor is calibrated to provide an electrical current proportional to an amount of alcohol detected in a breath sample. An adapter removably connects the replaceable sensor module to the breathalyzer and transmits the electrical current generated by the alcohol sensor to the processor for processing. The alcohol sensor and the adapter is mounted on a printed circuit board to provide the replaceable alcohol sensor module. The processor measures the electrical current and calculates a blood alcohol concentration of the breath sample based on the electrical current measured by the alcohol sensor. The calculated blood alcohol concentration is display on the display. The processor, the replaceable alcohol sensor module, and the display is housed in the housing to provide the breathalyzer.

In accordance with an exemplary embodiment of the claimed invention, a breathalyzer comprises a processor, a replaceable alcohol sensor module, a display and a housing. An alcohol sensor that is calibrated to provide a change in its resistivity based an amount of alcohol detected in a breath sample. An adapter removably connects the replaceable sensor module to the breathalyzer and transmits the change in the resistivity of the alcohol sensor to a processor of the breathalyzer for processing. The alcohol sensor and the adapter is mounted on a printed circuit board to provide the replaceable sensor module. The processor calculates a blood alcohol concentration of the breath sample based on the change in the resistivity of the alcohol sensor. The calculated blood alcohol concentration is displayed on the display. The processor, the replaceable alcohol sensor module, and the display is housed in the housing to provide the breathalyzer.

Various other objects, advantages and features of the claimed invention will become readily apparent from the ensuing detailed description, and the novel features will be particularly pointed out in the appended claims.

BRIEF DESCRIPTION OF FIGURES

The following detailed descriptions, given by way of example, and not intended to limit the claimed invention solely thereto, will be best be understood in conjunction with the accompanying figures:

DETAILED DESCRIPTION OF THE EMBODIMENTS

Figure 1:
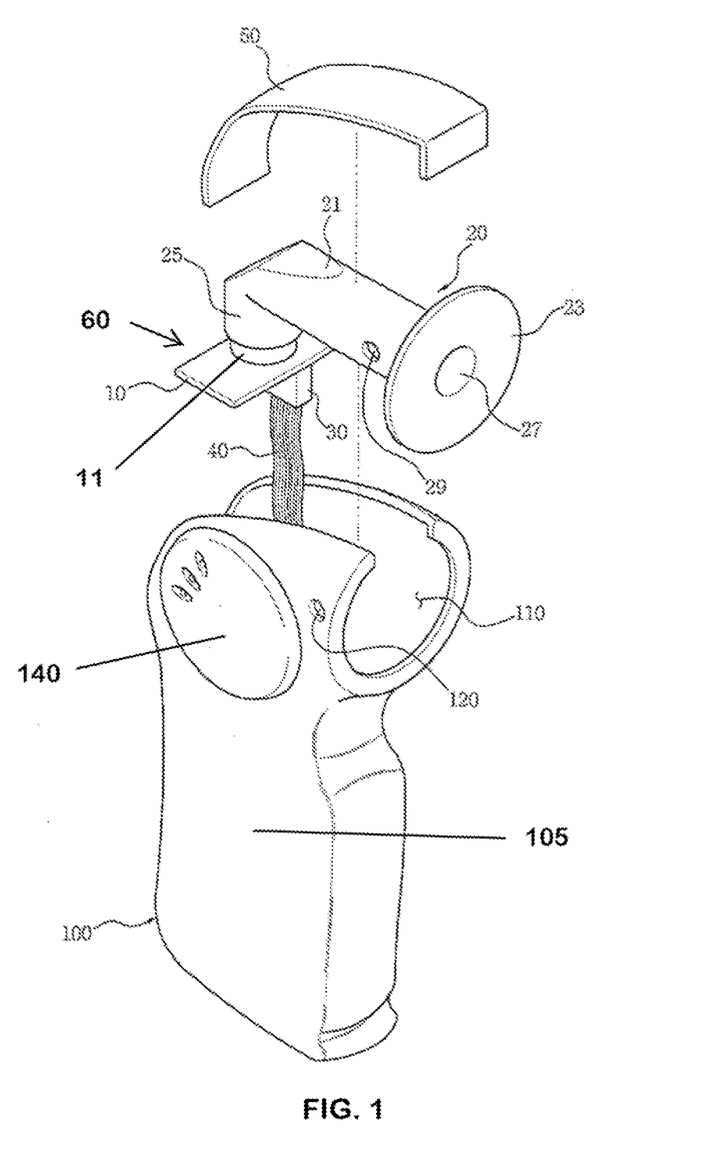
FIG. 1 is a diagram illustrating a breathalyzer unit incorporating a calibrated replaceable alcohol sensor module in accordance with an exemplary embodiment of the claimed invention.
Figure 2:
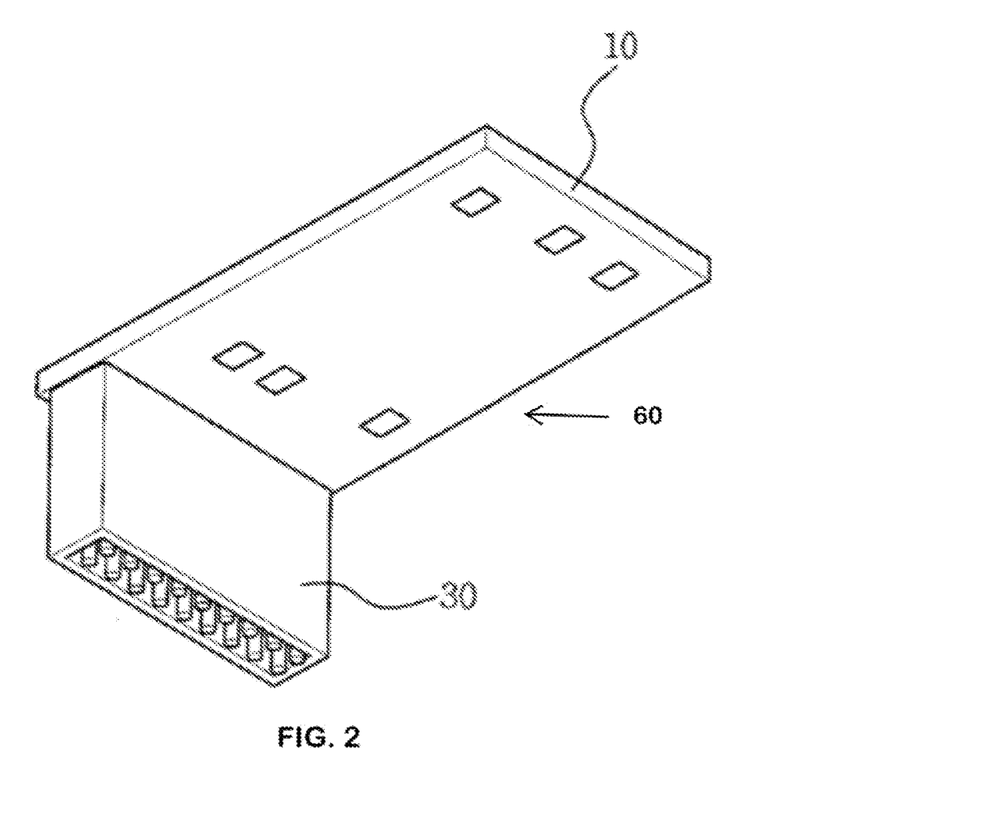
FIG. 2 is a diagram of a calibrated replaceable alcohol sensor module in accordance with an exemplary embodiment of the claimed invention.
Figure 4:
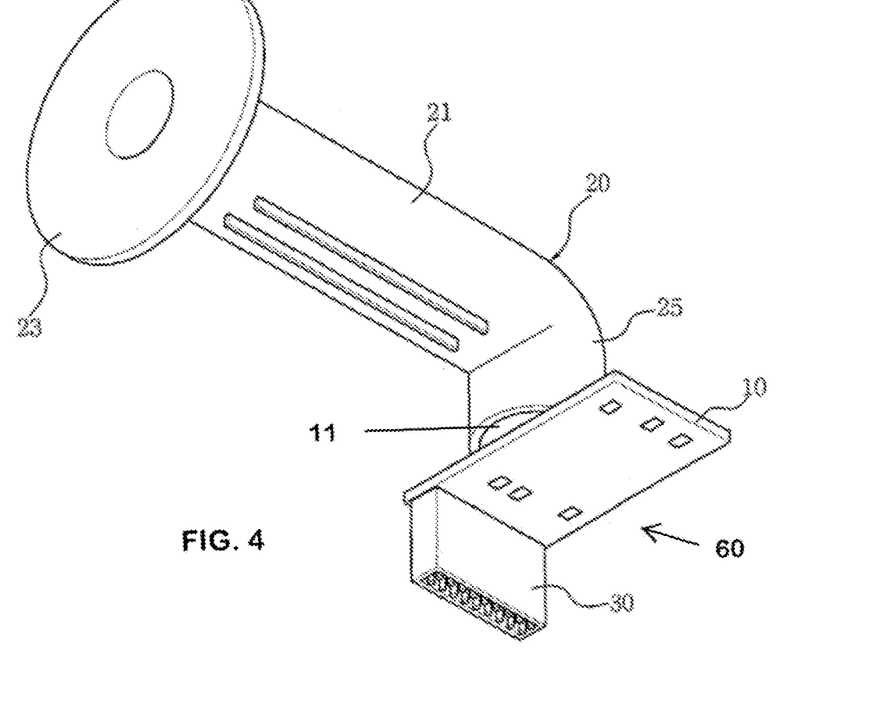
FIG. 4 is a diagram of a calibrated replaceable alcohol sensor module attached to a breath sampling tube in accordance with an exemplary embodiment of the claimed invention.

In order to eliminate the aforementioned problems with current recalibration methods, the sensor module 60 of the claimed invention is made compatible with a wide assortment of breathalyzers 100, as shown in FIG. 1. Breathalyzers 100 can be newly manufactured, or modified, with an easily accessible compartment 110 for both the installation and removal of the calibrated breath alcohol sensor module 60 of the claimed invention. In accordance with an exemplary embodiment of the claimed invention, the accessible compartment 110 comprises a system to attach and secure the sensor module to the body of the breathalyzer 100 (e.g. attachment slots or fasteners 120), an interface 40 to electronically link the breathalyzer 100 to the adapter 30 of the sensor module 60, and a cover or faceplate 50 to enclose the sensor module 60 once it is secured within the body of the breathalyzer 100. In addition, a breath sampling tube 20 can be attached to the sensor module 60, as shown in FIGS. 1 and 4, for those breathalyzers 100 requiring the breath sampling tube 20 for the breath alcohol sensor 11 to function properly. As a matter of compatibility and convenience, the claimed invention describes the sensor module 60 and the breath sampling tube 20 as separate components, because of the inevitable variation in and/or non-use of the breath sampling tubes 20 across various types of breathalyzer 100. However, "calibrated replaceable alcohol sensor module" or "sensor module" 60 may refer to the claimed invention with or without the attached breath sampling tube 20, with or without the memory 15, and with or without the heating unit 13.

Figure 3:
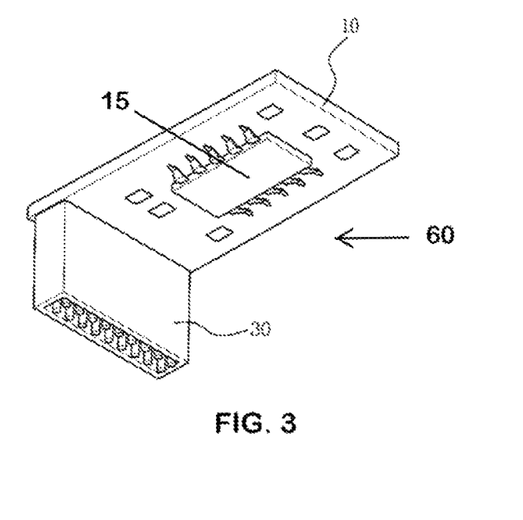
FIG. 3 is a diagram of a calibrated replaceable alcohol sensor module with memory in accordance with an exemplary embodiment of the claimed invention.
Figure 5:
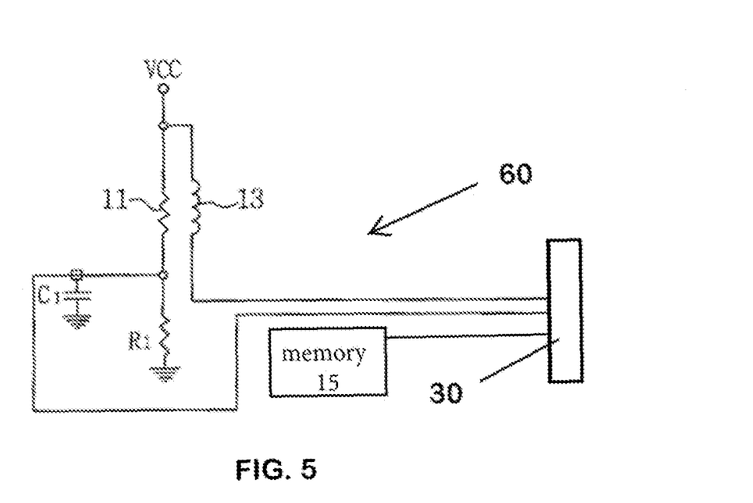
FIG. 5 is a diagram illustrating the primary circuitry of the sensor module in accordance with an exemplary embodiment of the claimed invention.

Turning now to FIGS. 2-6, there is illustrated a sensor module 60, in accordance with an exemplary embodiment of the claimed invention, comprising a printed circuit board (PCB) 10, an alcohol sensor 11 and an adapter 30 to electrically/electronically link the sensor module to a breathalyzer 100. The adapter 30 of the sensor module 60 communicates the sensor reading from the alcohol sensor 11 to the breathalyzer 100. In accordance with exemplary embodiment of the claimed invention, as shown in FIGS. 3-5, the sensor module 60 can additional comprise a non-volatile memory unit 15, a heating unit 13 and/or a breath sampling tube 20.

In accordance with an exemplary embodiment of the claimed invention, the circuitry of the alcohol sensor 11 of the sensor module 60 is operable to detect changes in conductivity according to varying levels of alcohol concentration. The alcohol sensor 11 can be a fuel cell sensor, a semiconductor sensor and the like. For example, a fuel cell sensor has a porous acid-electrolyte material between two platinum electrodes. As the breath sample flows past the fuel cell, the platinum oxidizes the alcohol in the breath sample to produce acetic acid, protons and electrons. The electrons flows from the platinum electrode of the alcohol sensor 11 to provide an electrical current, which is transmitted to the signal processing unit 150 of the breathalyzer 100 via the adapter 30 of the alcohol sensor 11. The electrical current produced by the alcohol sensor 11 is proportional to the amount of alcohol in the breath sample that is oxidized by the alcohol sensor 11. The processor or signal processing unit 150 of the breathalyzer 100 measures the electrical current and calculates BAC. The display 140 of the breathalyzer displays the calculated BAC.

A semiconductor sensor is generally formed from a metal oxide, e.g., tin oxide. When a voltage is applied to the semiconductor sensor without any sample, it produces a small output current. But, when alcohol, i.e., ethanol molecules, from the breath sample contacts the metal oxide, it changes the resistivity of the metal oxide, thereby altering the current outputted by the semiconductor sensor. That is, when the ethanol molecules comes in contact with the metal oxide of the semiconductor sensor, the reaction changes the resistivity of the semiconductor sensor. The semiconductor sensor measures the changes in the resistivity caused by the breath sample. Such changes in the resistivity results in change in the output current, hence the semiconductor-based breathalyzer can measure the change in the resistivity or change in the current to calculate/estimate the BAC.

Figure 6:
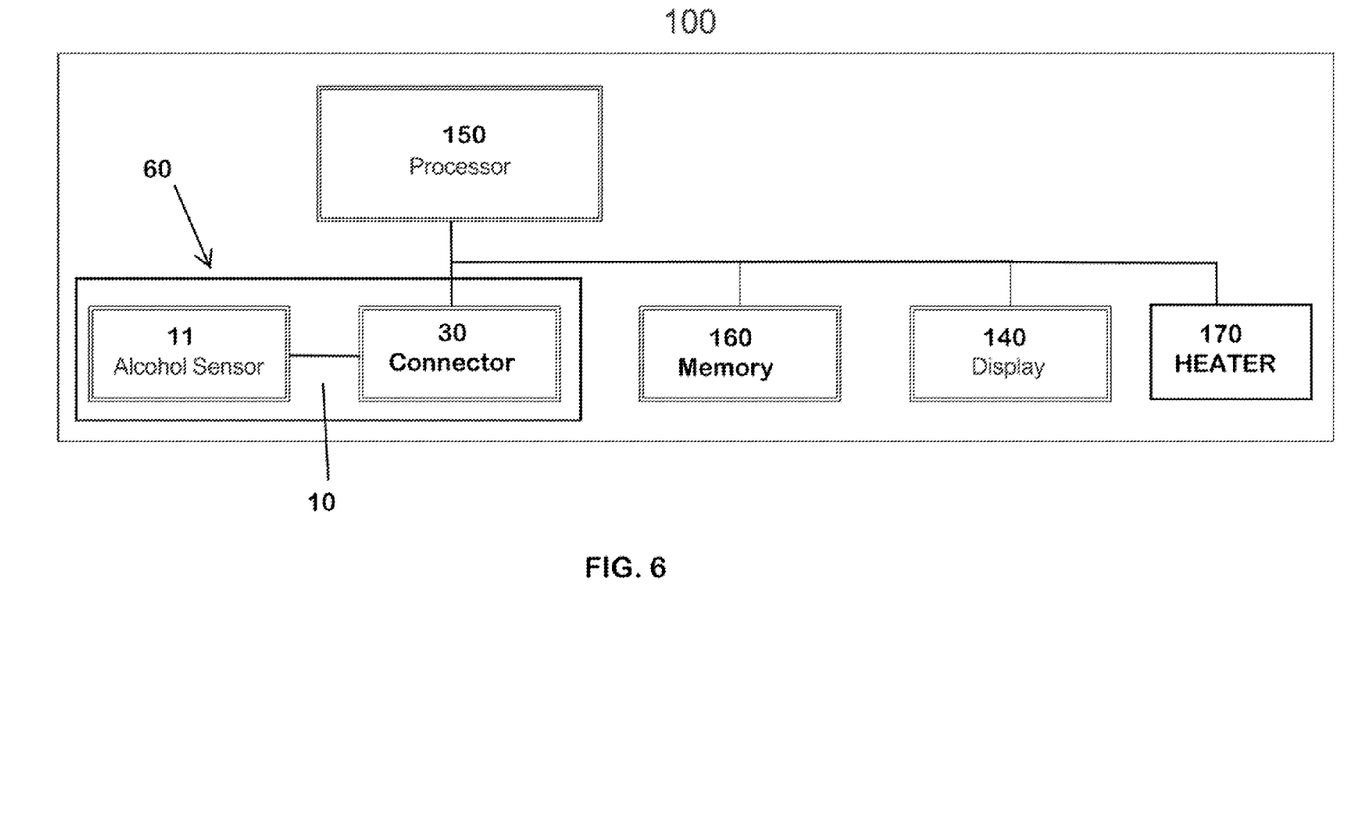
FIG. 6 is block diagram of the breathalyzer incorporating a calibrated alcohol sensor module in accordance with an exemplary embodiment of the claimed invention.
Figures 7A, 7B, 7C, 7D:
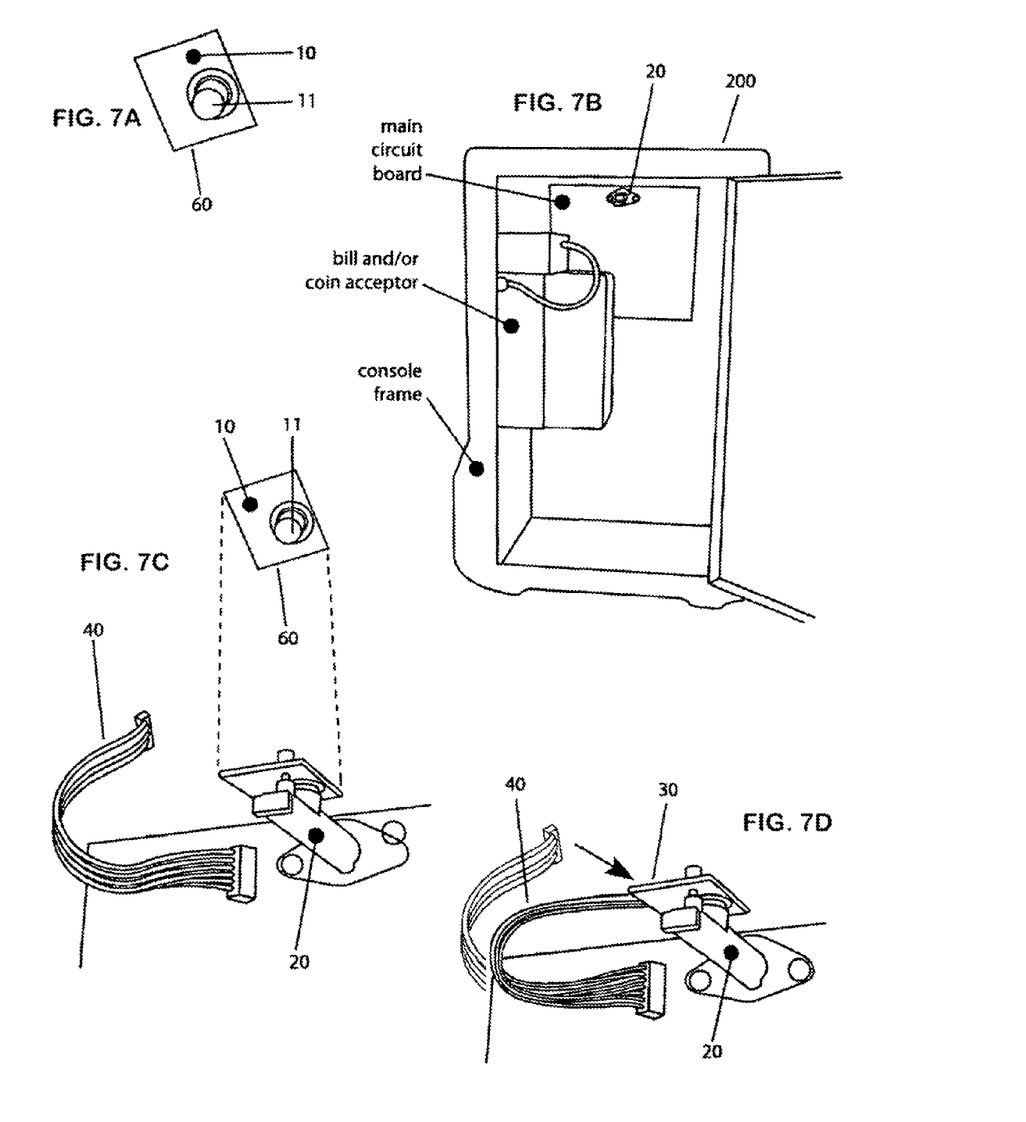
FIGS. 7A-7D are diagrams of a calibrated replaceable alcohol sensor module as incorporated in a coin-operated breathalyzer in accordance with an exemplary embodiment of the claimed invention.

It is appreciated that certain alcohol sensor 11, e.g., a semiconductor sensor, needs to be warmed up to a predetermined temperature before use to provide accurate readings. For those breathalyzers 100 with such alcohol sensor 11, the optional heating unit 13 to warm the alcohol sensor 11 can be provided on the sensor module 60 or the optional heater 170 to warm the alcohol sensor 11 can be equipped in the breathalyzer 100. The adapter 30 communicates data and readings to the breathalyzer 100.

Returning to FIG. 5, in accordance with an exemplary embodiment of the claimed invention, signals from the sensor module 60 to the breathalyzer's processor or signal processing unit 150 and the data from the non-volatile memory 15 is sent through the adapter 30. The adapter 30 connects the sensor module 10 to the breathalyzer 100, or as shown in FIG. 1, the adapter 30 connects the sensor module 10 to the breathalyzer 100 via the cable 40. In accordance with an exemplary embodiment of the claimed invention, the sensor module 60 can include all components of a breathalyzer 100 that may suffer from residue build-up and other problems requiring re-calibration. This advantageously enables the claimed invention to provide a breathalyzer 100 that is as accurate as and functionally equivalent to a "new" breathalyzer 100 by simply replacing the sensor module 60 of the claimed invention.

The primary cause for breathalyzer inaccuracy is sensor pollution, which refers to the build-up of sensor contaminants such as saliva, cigarette smoke, food particles, etc. This buildup of contaminants does not only cause sensor inaccuracy, but also reduces the overall lifetime of the sensor 11, because the residue cannot simply be removed. This means that even if the sensor is re-calibrated or adjusted, it can never be as efficient or accurate as a new sensor 11. The buildup of contaminants within the breath sampling tube 20 can also affect functionality and accuracy of the breath alcohol sensor 11, but to a lesser extent than sensor pollution.

In accordance with an exemplary embodiment of the claimed invention, the breath sampling tube 20 attaches to the sensor module 60, as shown in FIGS. 1 and 4. The breath sampling tube 20 is attached directly above the alcohol sensor 11, so that the alcohol sensor 11 can process alcohol readings from a breath sample.

As can be seen in FIGS. 1 and 4, in accordance with an exemplary embodiment of the claimed invention, the breath sampling tube 20 consists of a long cylindrical tube 21 for the blown air to travel through, a mouthpiece slot 27, and a bent or curved section 25 to direct air toward the alcohol sensor 11. Although, the breath sampling tube 20 is shown as long cylindrical bent tube, it is appreciated that it can be any shape or length to accommodate different types of breathalyzers.

In accordance with an exemplary embodiment of the claimed invention, FIG. 1 shows how the calibrated replaceable breath alcohol sensor module 60 can be installed into a compatible breathalyzer 100. The breath sampling tube 20 of the breathalyzer 100 is attached to the sensor 11 of the sensor module 60. The breath sampling tube 20 comprises an attachment slot 29 and the breathalyzer 100 comprises an attachment slot 120 to secure the sensor module 60 in the accessible compartment 110 of the breathalyzer 100. Although a cable 40 is shown in FIG. 1 to link the sensor module 60 to the breathalyzer's signal processing unit 150 via the adapter 30, the adapter 30 can link the sensor module 60 directly to the breathalyzer's signal processing unit 150. The attachment slots 29, 120 can be secured using screws, pins or other known fastening means. The breathalyzer 100 also comprises a cover 50 for enclosing the sensor module 60 after installation to maintain a consistent exterior appearance of the breathalyzer 100.

Typically, the user purchases the breathalyzer 100 for work (e.g., a police officer can use it for sobriety testing), clinical studies, personal use, etc. After many repeated uses, the breathalyzer 100 generally requires re-calibration due to residue build-up and/or other problems discussed herein. If the breathalyzer 100 is requires re-calibration, the user contacts the retailer and the retailer directs the user to an appropriate service center. The user ships the breathalyzer 100 to the service center. Upon receipt of the breathalyzer 100, the service center calibrates the breathalyzer, e.g., using the simulation system, and ships the re-calibrated breathalyzer back to the user, thereby enabling the user to use the breathalyzer 100 to calculate or measure BAC.

Typically, the breathalyzer 100 requires re-calibration after being used for 200-300 times (varying depend on the factors noted herein). Alternatively, the alcohol sensor module 60 or the signal processing unit 150 of the breathalyzer 100 can perform tests periodically or upon request by the operator (i.e., pressing a button on the housing 105 of the breathalyzer 100) to determine if the breath alcohol sensor 11 requires re-calibration. If the breathalyzer 100 requires re-calibration, the user can purchase calibrated sensor module 60 of the claimed invention. Alternatively, the user can purchase the calibrated sensor module 60 over the phone or internet and the retailer ships a new calibrated sensor module 60 to the user. The user installs the new calibrated sensor module 60 in the breathalyzer 100, thereby enabling the user to use the breathalyzer 100 to calculate or measure BAC. It is appreciated that the user can pre-purchase the new calibrated sensor module 60 to replace the existing replaceable sensor module, thereby eliminating any downtime with the breathalyzer 100.

It is appreciated that the user can purchase additional new calibrated sensor module(s) 60 along with the breathalyzer 100. Also, the user can purchase the new calibrated sensor module 60 after the purchase of the breathalyzer 100 but before the breathalyzer 100 requires calibration. If the breathalyzer 100 requires re-calibration, the user installs the new calibrated sensor module 60 in the breathalyzer 100, thereby enabling the user to use the breathalyzer 100 to calculate or measure BAC.

It is appreciated that installation procedure will vary for different types of breathalyzers 100, e.g., breathalyzers without a breath sampling tube 100 and/or without a cable 40. The user can prepare an exemplary breathalyzer 100 with the breath sampling tube 20 and cable 40, as shown in FIG. 1, for installation of a calibrated alcohol sensor module 60 in the breathalyzer 100. The user can use a flat, sharp tool to carefully open the top cover 50 of the breathalyzer 100, and lifts the breath sampling tube 20 to access the alcohol sensor module 60. Next, the user removes the breath sampling tube 20, and then carefully raises the alcohol sensor module 60 from the body of the breathalyzer 100, taking care not to detach the cable 40 from the body of the breathalyzer 100. The cable 40 is removed from the adapter or slot 30 underneath the alcohol sensor module 60. It is appreciated that certain type of breathalyzers do not require a cable 40 and an adapter 40 connects directly to the breathalyzer without the cable 40. The cable 40 is inserted into the new alcohol sensor module 60 and the alcohol sensor module 60 is placed in its original position in the breathalyzer. The breath sampling tube 20 is then reattached directly on to the alcohol sensor module 60 and the cover 50 is reattached onto the top of the body of the breathalyzer 100.

Figures 8A, 8B:
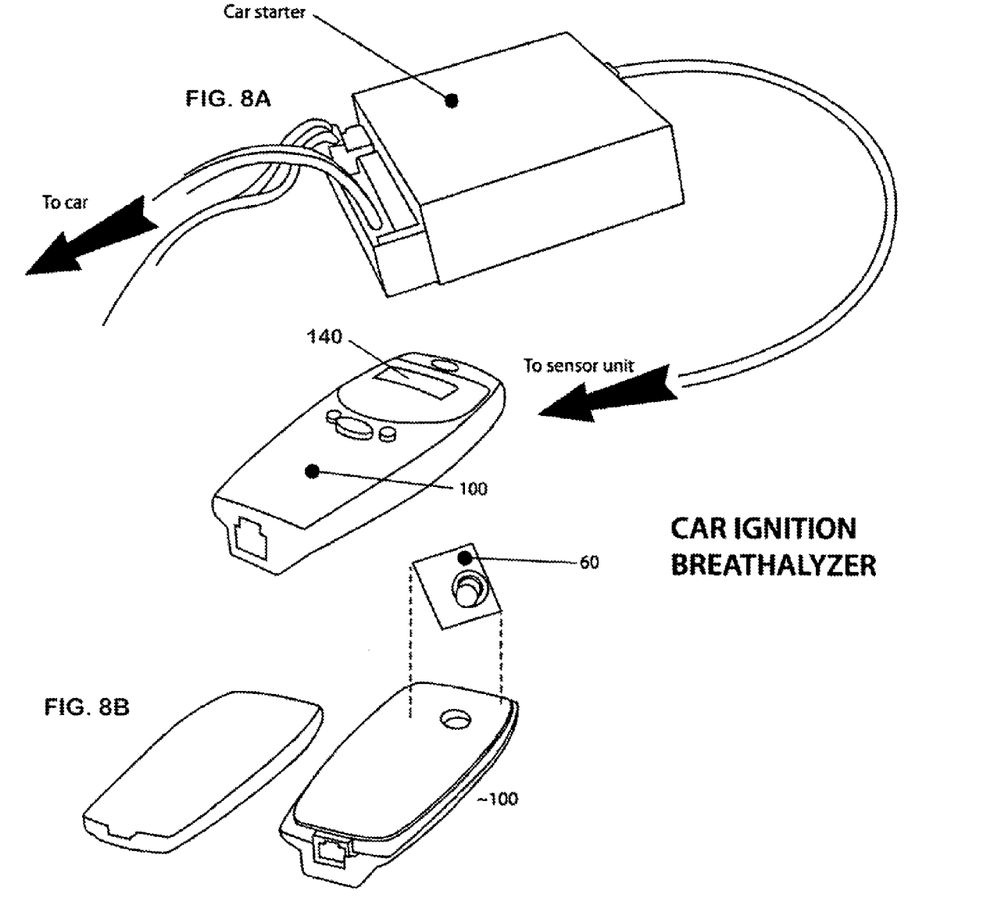
FIGS. 8A-8C are diagrams of a calibrated replaceable alcohol sensor module as incorporated in a car ignition breathalyzer in accordance with an exemplary embodiment of the claimed invention.
Figure 8C:
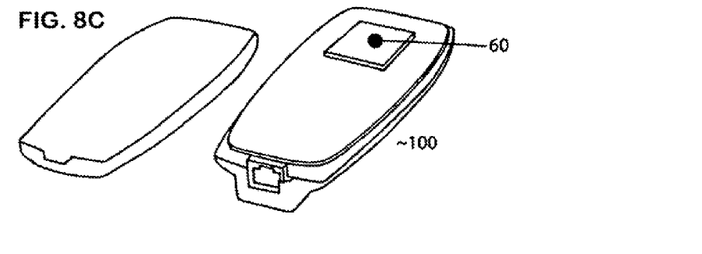
Figure 9A:
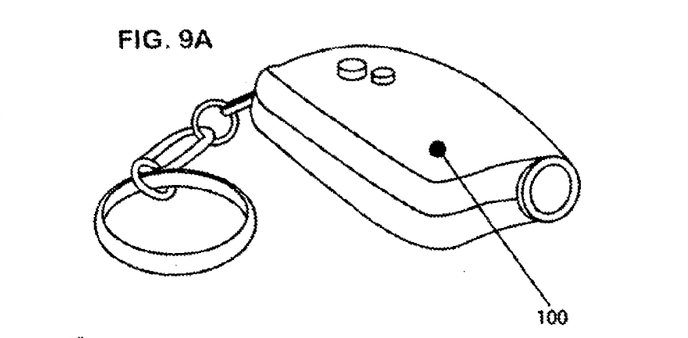
FIGS. 9A-9C are diagrams of a calibrated replaceable alcohol sensor module as incorporated in a key-chain breathalyzer in accordance with an exemplary embodiment of the claimed invention.
Figure 9B:
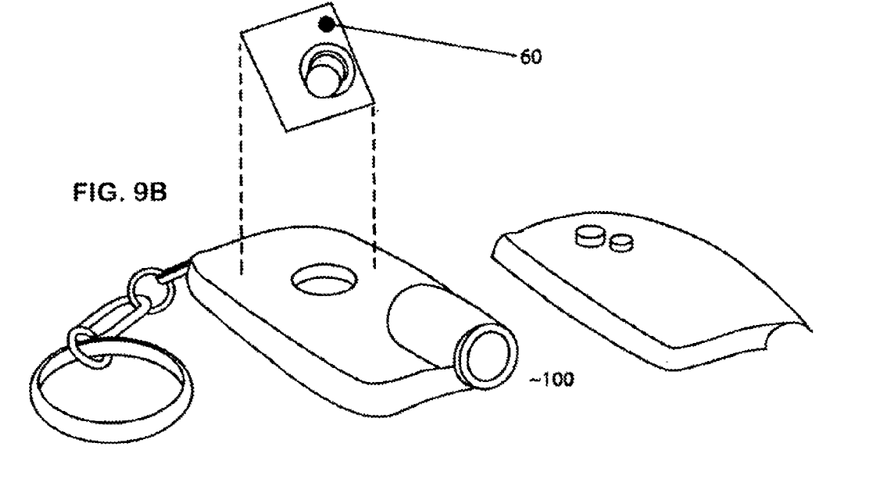
Figure 9C:
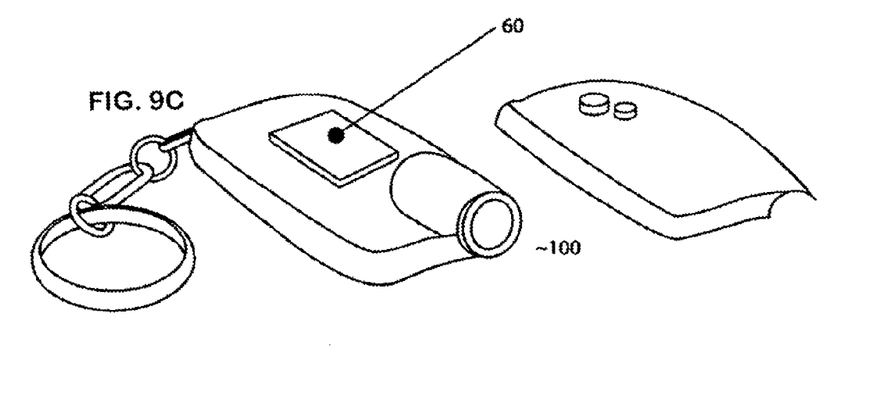

The claimed invention, having been described, will make apparent to those skilled in the art that the same may be varied in many ways without departing from the spirit and scope of the invention. Any and all such modifications are intended to be included within the scope of the following claims. For example, FIG. 1 shows distinct and defined locations for components such as attachment slots 29, 120 and cover 50, but as breathalyzers 100 are manufactured in many different styles and shapes, only one example of how the calibrated sensor module 60 of the claimed invention is installed in a particular breathalyzer (or the fitment of the calibrated sensor module 60 to a particular breathalyzer) is shown for simplicity. It is appreciated that the claimed invention is not limited to the breathalyzer 100 example given in FIG. 1, either in terms of fitment, attachment methods or specific installation/removal procedures. Other types of breathalyzers include, for example, portable breathalyzers, coin-operated commercial units (FIGS. 7A-7D), key-chain breathalyzers (FIGS. 9A-9C) and car ignition breathalyzers (FIGS. 8A-8C). The replaceable breath alcohol sensor module 60 of the claimed invention is intended for use in all such varieties of breathalyzers.

The invention of claimed is:

1. A replaceable alcohol sensor module for use with a breathalyzer comprising:
   an alcohol sensor that is calibrated to provide an electrical current proportional to an amount of alcohol detected in a breath sample;
   an adapter to removably connect the replaceable sensor module to the breathalyzer and to transmit the electrical current generated by the alcohol sensor to a processor of the breathalyzer for processing, the processor measures the electrical current and calculates a blood alcohol concentration of the breath sample based on the measured electrical current;
   a printed circuit board to mount the alcohol sensor and the adapter; and
   wherein the replaceable alcohol sensor module is installable in the breathalyzer to replace existing replaceable alcohol sensor module in the breathalyzer after being used for a predetermined number of times.

2. The replaceable alcohol sensor module of claim 1, further comprising a non-volatile memory unit to store information to maintain the alcohol sensor in a calibrated state.

3. The replaceable alcohol sensor module of claim 1, wherein the breathalyzer is one of the following: a portable breathalyzer, a coin-operated breathalyzer, a key-chain breathalyzer or a car ignition breathalyzer.

4. The replaceable alcohol sensor module of claim 1, wherein the alcohol sensor is a fuel cell sensor.

5. The replaceable alcohol sensor module of claim 1, further comprising a breath sampling tube to receive and direct the breath sample to the alcohol sensor.

6. A breathalyzer comprising a replaceable alcohol sensor module of claim 1, the processor, a display to display the calculated blood alcohol concentration, and a housing to house the processor, the replaceable alcohol sensor module, and the display.

7. A replaceable alcohol sensor module for use with a breathalyzer comprising:
   an alcohol sensor that is calibrated to provide a change in its resistivity based an amount of alcohol detected in a breath sample;
   an adapter to removably connect the replaceable sensor module to the breathalyzer and to transmit the change in the resistivity of the alcohol sensor to a processor of the breathalyzer, the processor calculates a blood alcohol concentration of the breath sample based on the change in the resistivity of the alcohol sensor;
   a printed circuit board to mount the alcohol sensor and the adapter; and
   wherein the replaceable alcohol sensor module is installable in the breathalyzer to replace existing replaceable alcohol sensor module in the breathalyzer after being used for a predetermined number of times.

8. The replaceable alcohol sensor module of claim 7, wherein the alcohol sensor provides an electrical current based the change in the resistivity of the alcohol sensor; and wherein the processor measures a change in the conductivity of the alcohol sensor based on the electric current to calculate the blood alcohol concentration of the breath sample.

9. The replaceable alcohol sensor module of claim 7, further comprising a non-volatile memory unit to store information to maintain the alcohol sensor in a calibrated state.

10. The replace alcohol sensor module of claim 7, wherein the breathalyzer is one of the following: a portable breathalyzer, a coin-operated breathalyzer, a key-chain breathalyzer or a car ignition breathalyzer.

11. The replaceable alcohol sensor module of claim 7, further comprising a breath sampling tube to receive and direct the breath sample to the alcohol sensor.

12. The replaceable alcohol sensor module of claim 7, wherein the alcohol sensor is a semiconductor sensor.

13. The replaceable alcohol sensor module of claim 7, further comprising a heating unit to warm up the alcohol sensor to a predetermined temperature.

14. The replaceable alcohol sensor module of claim 7, wherein the alcohol sensor is warmed up to a predetermined temperature by a heating unit of the breathalyzer.

15. A breathalyzer comprising a replaceable alcohol sensor module of claim 7, the processor, a display to display the calculated blood alcohol concentration, and a housing to house the processor, the replaceable alcohol sensor module, and the display.

* * * * *